(12) United States Patent
Khavinson et al.

(10) Patent No.: US 6,642,201 B1
(45) Date of Patent: Nov. 4, 2003

(54) USE OF A DIPEPTIDE FOR STIMULATING REPAIR PROCESSES

(75) Inventors: Vladimir Khatskelevich Khavinson, St-Petersburg (RU); Vyacheslav Grigorievich Morosov, Leningradskaya obl (RU); Vladimir Viktorovich Malinin, St-Petersburg (RU); Sergei Vladimirovich Sery, Leningradskaya obl (RU)

(73) Assignee: Obschestvo S Ogranichennoi Otvetstven Nostiji "Klinika Instituta Bioregulyatsii Gerontologii", St. Petersburg (RU)

( * ) Notice: Subject to any disclaimer, the term of this patent is extended or adjusted under 35 U.S.C. 154(b) by 0 days.

(21) Appl. No.: 09/720,519
(22) PCT Filed: May 27, 1999
(86) PCT No.: PCT/RU99/00188
§ 371 (c)(1), (2), (4) Date: Feb. 21, 2001
(87) PCT Pub. No.: WO99/66948
PCT Pub. Date: Dec. 29, 1999

(30) Foreign Application Priority Data

Jun. 23, 1998 (RU) ............................................ 98111342

(51) Int. Cl.$^7$ .......................... A61K 38/05; C07K 5/068
(52) U.S. Cl. ............................ 514/2; 514/19; 424/464; 424/489
(58) Field of Search .................. 514/2, 19; 424/464, 424/489

(56) References Cited

FOREIGN PATENT DOCUMENTS

| EP | 0 165 492 | 12/1985 |
| RU | 2080120 | 5/1997 |
| WO | WO 95/03067 | * 2/1995 |

OTHER PUBLICATIONS

Liu et al. 'Transplants of Fibroblast Genetically Modified to Express BDNF Promote Regeneration of Adult Rat Rubrospinal Axons and Recovery of Forelimb Function.' J. of Neurosci. vol. 19, No. 11, pp. 4370–4387, 1999.*

Ehrman et al. 'Lack of Regulation on the Heart Forming Region of Avian Embryos' Developmental Biol. vol. 207, pp. 163–175 1999.*

Maden et al. 'Retinoic Acid, A Regeneration–Inducing Molecule' Developmental Dynamics, vol. 226, pp. 237–244. 2003.*

* cited by examiner

Primary Examiner—Brenda Brumback
Assistant Examiner—Anish Gupta
(74) Attorney, Agent, or Firm—Whitham, Curtis & Christofferson, P.C.

(57) ABSTRACT

L-Lys-L-Glu dipeptide is proposed for use in medicine for preparation of a drug capable of stimulating repair processes. According to the invention, the pharmaceutical peptide preparation capable of stimulating regeneration consists of pharmaceutically admissible carrier and effective quantity of dipeptide as an active part, which is a combination of, L-lysil-L-glutamic acid or its salts.

The pharmaceutical peptide preparation is proposed for parenteral, intranasal oral and local application.

According to the invention, the method stimulating regeneration consists of prophylactic and/or treatment injections of the drug in the dose of 0.01–100 μkg per per 1 kg of weight, at least once a day during a period necessary for obtaining a therapeutic effect.

8 Claims, 4 Drawing Sheets

Figure 1 a.

PCNA-positive nuclei of proliferating cells in the generative crypt zone of the duodenum. Avidin-biotin-peroxydase method – x 100. Irradiated animals.

Figure 1 b.

PCNA-positive nuclei of proliferating cells in the generative crypt zone of the duodenum. Avidin-biotin-peroxydase method – x 100. Irradiated animals + L-Lys-L-Glu dipeptide.

Figure 2a.

Serotonin-immunopositive cells in the mucous membrane of the duodenum.
Streptavidin-biotin-peroxydase method – x 100. Irradiated animals.

Figure 2b.

Serotonin-immunopositive cells in the mucous membrane of the duodenum.
Streptavidin-biotin-peroxydase method – x 100. Irradiated animals + L-Lys- L-Glu dipeptide.

Figure 3a.

Metallotionein-immunopositive cells in the mucous membrane of the duodenum (histotopographic localization of MTL-positive cells). Streptavidin-biotin-peroxydase method – x 100. Irradiated animals.

Figure 3b.

Metallotionein-immunopositive cells in the mucous membrane of the duodenum (histotopographic localization of MTL-positive cells). Streptavidin-biotin-peroxydase method– x 400. Irradiated animals + L-Lys- L-Glu dipeptide.

Figure 4a.

Mast cells in the duodenum mucous membrane.Selective staining with toluidin blue, pH 0,5 –x 100. Irradiated animals.

Figure 4b.

Mast cells in the duodenum mucous membrane.Selective staining with toluidin blue, pH 0,5 –x 100. Irradiated animals + L-Lys- L-Glu dipeptide.

USE OF A DIPEPTIDE FOR STIMULATING REPAIR PROCESSES

BACKGROUND OF THE INVENTION

1. Field of the Invention

The invention is related to pharmacology, i.e. pharmaceuticals containing peptides and their compositions, which may find prophylactic and/or therapeutic employment in medicine as stimulators of tissue regeneration in case of pyo-inflammatory diseases; and post-operative complications, trophic disorders, diseases and injuries of skin and mucous membrane, consequences of radiation, thermal and chemical factors accompanied by the disturbances of repair processes.

The invention is concerned with application of dipeptide L-lysil-L-glutamic acid(L-Lys-L-Glu) as a substance stimulating repair processes in subjects, which need it.

2. Background Description

Among the drugs most analogous in application to the invented one there is a group of preparations stimulating metabolic processes: derivatives of pirimidine (Methyluacil, Pentoxyl) and biogenic preparations (Actovegin, Solcoseryl) (1).

Methyluracil drawback consists in cutaneous allergic reactions (urticaria eruption), sometimes headaches and dizziness. Pentoxyl oral application may induce dyspepsia due to irritating action of the drug. The detriment of Actovegin and Solcoseryl consists in a small amount of active substances in the drugs, prolonged treatment and limited application with respect to the stage of the wound process, as well as low efficacy in treatment of purulent wounds. These drugs produce largely stimulating effect on leukopoiesis.

There is known dipeptide L-Lys-L-Glu used as a component for peptide synthesis (2).

It is well known that L-Lys-L-Glu dipeptide displays immunomodulating activity (3). However, this activity of the dipeptide characterizes only the direction of its immunobiologcal action,. which is not an obvious and interrelated manifestation of the dipeptide properties with respect to the repair process, and does not specify indications for its clinical application. Below given examples of dipeptide L-Lys-L-Glu stimulating action on repair processes confirm objectively the absence of correlation between the known property and the claimed one.

SUMMARY OF THE INVENTION

The claimed invention is aimed at the solution of the problem of obtaining the substance of peptide origin capable of stimulating repair processes.

With respect to the invention, it is proposed to use a dipeptide with the following amino acid sequence: L-Lys-L-Glu, as a substance revealing a property to stimulate repair processes.

Dipeptide is obtained by a classical method of peptide synthesis in a solution (4).

This previously unknown property of L-Lys-L-Glu dipeptide to stimulate repair processes was found out in an experimental study.

With respect to the invention there is proposed a pharmaceutical peptide preparation able to stimulate regeneration which contains a pharmaceutically admissible carrier and an effective amount of dipeptide as an active basis representing a compound L-lysil-L-glutamic acid (L-Lys-L-Glu) or its chemical modification as salts.

With respect to the invention, pharmaceutical peptide preparation, stimulating repair processes, may contain salts according to amino group (acetate, hydrochloride, oxalate), or according to carboxyl groups (salts of metals—Natrium, Calcium, Lithium, Zinc, Magnesium and other organic and non-organic cations, for example ammonium triethylammonium.

The notion "pharmaceutical peptide preparation", used in this application, implies the employment of any drug form, containing various pharmaceutical derivatives of the dipeptide, which reveals a therapeutic effect in treatment of the diseases requiring stimulation of tissue regeneration.

The notion "effective amount", used in this application, implies the employment of such an amount of the active base, which in compliance with its quantitative indices of activity and toxicity, as well as with respect to the knowledge available, must be effective in this drug form. In order to obtain pharmaceutical compositions meeting the invention, the proposed dipeptide or its pharmaceutically applicable derivatives are blended as an active ingredient and a pharmaceutical carrier In accordance with accepted pharmacology methods of compounding.

The carrier may have various forms, which depend on the drug form of the preparation, desirable for administration, for example, parenteral, oral, intranasal or local (e.g. as applications or ointments).

All known pharmaceutical components may be used for preparation of compositions, in preferable doses, for oral or local application.

For parenteral (intranasal) administration, the carrier usually includes sterile water, although could be used other ingredients instrumental for stability or maintaining sterility.

In accordance with the invention, the dipeptide is active in case of its administration in doses 0.01–100 $\mu$kg/kg of the body weight, although lower (higher) doses, with respect to severity and character of the disease, could be used. The claimed pharmaccutical peptide preparation is proposed for parenteral, Intranasal, oral, and local application.

The invention embraces both method of stimulation of the regeneration processes for humans and animals who need such stimulation and pharmaceutical compositions for implementation of this method.

In accordance with the invention, the method of stimulation of the processes of regeneration by means of administration of the drug containing, as in active base, dipeptide L-lysil-L-glutamic acid (L-Lys-L-Glu) or its chemical modifications in the form of salts or other derivatives, is manifested in the activation of cell metabolism and the regulatory effect on the processes of proliferation and differentiation of cells of various tissues. The method includes prophylactic or therapeutic exposure of the subject which needs it, to the drug in doses 0.01–100 $\mu$kg/kg of the body weight at least once a day during the period necessary for reaching therapeutic effect—10–40 days with respect to the character and severity of the discase.

The invention involves prophylaxis and treatment of the diseases, which require stimulation of tissue regeneration: pyo-inflammatory processes, and post-surgical complications., trophic disturbances, skin and mucous diseases and lesions, after effects of radiation, thermal, and chemical factors, accompanied with the shift of repair processes.

BRIEF DESCRIPTION OF THE DRAWINGS

The foregoing and other objects, aspects and advantages of an exemplary embodiment of the invention will next be described in greater detail, with the aid of a drawing. Shown are.

DETAILED DESCRIPTION OF A PREFERRED EMBODIMENT OF THE INVENTION

The invention is illustrated by the examples of synthesis of the dipeptide with the formula L-lysil-L-glutamic acid (L-Lys-L-Glu) (example 1), those of the tests for toxicity and biological activity of the dipeptide (examples 2, 3, 4 and 5) and examples of the results of clinical application of the dipeptide, demonstrating its pharmacological properties and confirming the possibility The of reaching therapeutic effect (examples 6, 7, 8).

EXAMPLE 1

Synthesis of L-Lys-L-Glu Dipeptide

1. Nα, Nε—dibenzyloxycarbonyllizyl—γ—benzylgluthamine acid. 0.154 g (0.65 mmol) of γ—benzylgluthamine acid am suspended in 3 ml of dimethylphormamide and added 0.091 ml (0.65 mmol) of triotbylarnine while mixing, then 0.300 g (0.59 mmol) of N. Oxysuccinimide ether of Na, Nε—dibenzyloxyrarbonyllizyl. The reacted mixture is blended within 12 hours at room temperature. Afterwards the solvent is boiled down in the vacuum under 40° C., and 10 ml of In $H_2SO_4$, are added to the residue. The product is twice extracted by the ethyl acetate (30×2). The organic layer is bathed in In $H_2SO4$ and water up to neutral reaction and dried over $Na_2SO_4$. Solvent distillation is conducted under vacuum at 40° C. and the residue is dissolved in 1–2 ml of ethyl acetate. The product is set down by hexane and recrystallized in the system ethyl acetate/hexane. The product is filtered and dried under vacuum over. $P_2O_5$. The yield is 0.0330 g (88%). The coefficient of retaining Rf=0.81 (benzol:acetone is 1:1, silufol).

2. L-Lysil-L-Glutamic Acid.

Defended dipeptide [1] (0.330 g) is dissolved in 10 mg of methanol, added to 3 ml of water and hydrate over palladium on coal. The control is conducted by thin layer chromatography. Upon the completion of hydration the catalyst is filtered out and the residue is dissolved in a minimal quantity of water and set out by methanol. The product is filtered, bathed in ethanol, dried under vacuum over $P_2O_5$. The yield is 0.110 g (85%). Temperature of melting being 194–196° C. [α] $γ^{20}$=+20.00 (c=3.0; $H_2O$). Rf=0.54 (acetonyl:water 1:3, "Merk"). Electrophoresis: $E_{Gly}$=1.96; $E_{Lys}$=0.98 (1400 volt, 45 min., 20% acetic acid, "Watmann 3MM".

To obtain corresponding salts according to carboxyl group, free dipeptide is added to a calculated amount of water solution of hydroxide of the corresponding metal (NaOH, KOH, $ZnOH_2$, LiOH, $CaOH_2$, $MgOH_2$. $NH_4OH$). To obtain triethylammonium salt, the processing is conducted in the same way using triethylamine as a base.

EXAMPLE 2

Study of L-Lys-L-Glu Dipeptide Toxicity

The study of the general toxic activity of dipeptide L-Lys-L-Glu was conducted in compliance with "The rules of pre-clinical estimation of safety of pharmacological Substances (GLP)"—

The purpose of the study consisted of the identification of tolerable toxic doses of the drug, estimation of stage and character of pathological alterations in various organs and systems of the organism and determination of correlation between toxic effect related to dose and duration of drug application.

The estimation of acute toxicity of dipeptide L-Lys-L-Glu was conducted according to Kerber. The study was carried out on 66 white outbred male mice with body weight 20–23 g, kept under standard regimen and fed with standard chow in the vivarium. The animals were divided at random into 6 equal groups of 11 mice each. The animals were exposed to single administration of the drug intramuscularly, 0.25 ml in doses 1 mg/kg, 2 mg/kg, 3 mg/kg, 4 mg/kg, 5 mg/kg, several thousand times exceeding therapeutic dose recommended for clinical trial. Control animals were administered sodium chloride solution in the same amount.

In 72 hours and later on in 14 days, none of the animals in either of the groups died. No changes in the general state, behavior, locomotor activity, hairy or skin integument or physiological discharges were registered.

Thus, L-Lys-L-Glu dipeptide in doses several thousand times exceeding the therapeutic, recommended for clinical trials, does not induce any toxic effects, which points out wide therapeutic applicability of the drug.

The study of sub-acute toxicity of L-Lys-L-Glu dipeptide is carried out on 60 white outbred mice with body weight 150–250 mg. The animals of experimental groups were exposed daily to a single administration of the drug intramuscularly for 90 days in doses 1 mg/kg, 0.3 mg/kg, 3 mg/kg in 0.5 ml of sodium chloride solution. The animals of control groups were administered with sodium chloride solution in the same quantity.

During the whole period of Investigation the animals were under daily control. There was monitored animal behavior, as well as chow and water consumption, condition of hairy and mucous surfaces. The animals were weighed weekly. Morphological composition and properties of peripheral blood were studied prior to and an the $30^{th}$, $60^{th}$, and $90^{th}$ day of drug administration. Biochemical and coagulologic indices of the blood were studied upon experiment completion.

Chronic toxicity of L-Lys-L-Glu dipeptide obtained by the claimed method was studied during its longitudinal administration to rats with body weight 150–250 mg. The animals of experimental groups were exposed daily to single intramuscular administration of the substance in doses 1 mg/kg, 0.3 mg/kg, 3 mg/kg in 0.5 ml of sodium chloride solution for 6 months. There was analyzed animal behavior, as well as chow and water consumption, condition of hairy and of mucous surfaces. The animals were weighed daily during the first 3 months of the experiment and then once a month. In 3 months after the onset of administration and upon completion of the experiment hematological and biochemical examinations functions of cardiovascular system, liver, pancreas. kidney, and adrenal gland were conducted and estimated. Upon the termination of the drug administration some animals were exposed to pathomorphological examination with the purpose of studying the state of various departments of the brain and spinal marrow, heart, aorta, lungs, liver, organs of endocrine and immune systems.

The estimation of the general state of the animals, morphological and biochemical indices of peripheral blood, morphological state of intrinsic organs, cardio-vascular and respiratory systems, liver and kidney functions revealed no pathological changes in the organism.

The study of sub-acute and chronic toxicity of L-Lys-L-Glu dipeptide evidences the absence of side effects during long-term application of the drug in doses exceeding therapeutic one 100–1000 times.

EXAMPLE 3

Influence of L-Lys-Glu Dipeptide on the Healing of Purulent Incised Crushed Wounds of the Soft Tissues The efficacy of L-Lys-L-Glu dipeptide was estimated on the model of purulent incised crushed wounds of the femural soft tissues in shinshilla rabbits of both sexes with body weight 2–3 kg. Therefore, the rabbits underwent shaving in the area of femural soft tissues with subsequent incision 5 cm long and 2 sm deep. Soft tissues (muscles, subcutaneous fat) were crushed with Kocher 's forceps and infected with the pathogenic mixture Staphylococcus aureus, strain 186. Afterwards, the wound was sutured. In 72 hours the sutures were lifted; and the wound was treated with 3% solution of hydrogen peroxide.

The animals of experimental group were injected intramuscularly every day for five days with dipeptide L-Lys-L-Glu in a single dose 1 $\mu$kg per injection. Control rabbits were injected with sodium chloride solution according to the same scheme. In the process of treatment the wounds were treated with antiseptic remedies for external use.

The estimation of L-Lys-L-Glu dipeptide efficacy in the dynamics of the inflammatory process regression was based on the terms of crust rejection and wound clearance from the pyo-necrotic mass, and appearance of the granular tissue in the wound and beginning of edge epithelization. With the purpose of identifying objective criteria for the course of the wound process, indices reflecting semi-quantitative characteristics of separate cellular elements and structures of the granular tissue an days 6, 14, 21, 28 and 40 were analyzed. The activity of tissue enzymes was also estimated (5,6,7).

As a result of investigation it was registered that animals of all groups in the first phase of inflammation revealed on the $6_{th}$ day, extended necrosis in the tissues encircled with a thin rim of the granular tissue with diffused fresh fibroblasts and single histiocytes. In the phase of proliferation, small foci of necrosis were encircled with a wide layer of the granular tissue with an abundance of vessels and lymph calls. The amount of histiocytes increased and macrophages formed clusters in necrotic zones. Fibroblasts were stretched and had thin nuclei. Processes of cellular elements activation in animals of experimental group were especially pronounced(Table 1). In the phase of cicatrization these animals showed foci of necrosis encircled with the layer of the granular tissue with mature fibroblasts. Between fibroblasts there was noted the layer of collagenous fibres. Interstitial substance close to necrotic zones contained precollagenous fibres, fibroblasts, and histiocytes suggesting the process of resorption and substitution of necrotic tissues with fresh granular tissue.

A prominent feature of tissue response to the application of L-Lys-L-Glu dipeptide consisted in high activity of acid phosphatase in histiocytes in the phase of proliferation (14–28 days). In a few foci of leukocytory infiltration, as well as in the vascular endothelium, there was noted a high activity of alkaline phophotase. In the phase of cicatrization, a high content of acid phosphatase stabilized in histiocytes, and that of alkaline phosphatase—in leukocytes and vessels (Table 2).

The changes observed evidence intensification of cell metabolism in tissues, promoting fast clearance of the wound surface from necrotic tissues with subsequent wound epithelization (Table 3).

EXAMPLE 4

L-Lys-L-Glu Dipeptide's Influence on the Compensatory Regeneration of the Liver After Its Partial Hepatectomy The research has been conducted on 26 white outbred male rats weighing 150–200 grams. The animals were divided into thee following groups:

1 group—healthy animals;

2 group—control (rats which had undergone partial hepatectomy, with ⅔ of their liver ectomized);

3 group—rats which had undergone the operation and were subsequently (2 and 24 hours after the operation) administered two subcutaneous injections of L-Lys-L-Glu dipeptide (0,1 $\mu$kg per rat).

At the same time, the animals of the first and second groups were made injections of the same volume of the sodium hydrochloride. The extracted liver was preserved formalin.

The rats, which had been operated on, were killed by means of ether 32 and 96 hours after the operation. The rats from the control group were killed too, simultaneously. Their livers were preserved in formalin. After staining the preparations with hematoxilin-eosin, the mitotic index in the liver cells was defined, as well as the quantity of polyploid cells in the S-phase cell cycle (the quantity of dividing cells).

The study of mitotic activity of the regenerating liver cells 32 hours after a partial hepatectomy showed that the number of mitoses and cells in the S-phase of the cell cycle becomes two times bigger than in the liver of healthy animals. These differences are not reliable in the case of injecting the sodium hydrochloride, while after the L-Lys-L-Glu dipeptide injections, the increasing number of mitoses, DNA—synthesizing cells and the overall amount of dividing cells does become trustworthy.

The study of the liver preparation 96 hours after the hepatectomy proved that both, rats receiving the sodium hydrochloride and those injected with L-Lys-L-Glu dipeptide, demonstrated considerable intensification of mitotic activity of hepatocytes. Comparing the data of the third and second groups, it became. clear that the rats injected with L-Lys-L-Glu dipeptide had a number of mitoses twice as big as the rats injected with the sodium hydrochloride. The number of cells in the S-phase of their mitotic cycle of the third group of rats did not differ reliably from the number of hepatocytes in the S-phase of the second group, though, on the whole, the number of dividing cells, 96 hours after the hepatectomy in the regenerating liver of the rats injected with L-Lys-L-Glu dipeptide, was 75% bigger than with rats injected with the sodium hydrochloride (table 4).

Thus, it has been proved that the rats, injected with L-Lys-L-Glu dipeptide 96 hours after the partial hepatectomy, demonstrated intensification of the mitotic activity of hepatocytes, testifying to the acceleration of reparative processes In the liver.

EXAMPLE 5

Influence of L-lys-L-Glu Dipeptide an Regeneration of the Intestinal Mucous Membrane After the Radiation Injury The work has been performed on 24 two-month-old white male rats of the Wistar line, weighing 90–100 grams. The following three groups of animals were researched;

1 group—healthy animals;
2 group—control (irradiated animals);
3 group—irradiated animals injected with L-Lys-L-Glu dipeptide.

A general single γ—irradiation of 6 Gy, inducing "the syndrome of intestinal death", was made by the cobalt apparatus GUB 20000, with the dose capacity of 200 rad/min.

L-Lys-L-Glu dipeptide was injected 24 hours after the irradiation—0.5 µkg in 0.5 ml of the sodium hydrochloride—intraperitoneally during 5 days. The animals from the first and second groups received the sodium hydrochloride by the same scheme.

The study of L-Lys-L-Glu dipeptide's action has been performed on the proximal section of the duodenum of irradiated animals. The animals were killed under nembutal narcosis (50 mg/kg on the $8^{th}$ day after irradiation (beginning of the period of repair regeneration). Pieces of the duodenum were being preserved during 24 hours by Karnovsky for the electronic microscopy.

The ultra-structural research was conducted under the JEM-100S microscope (JEOL, Japan) at the ultra-thin microscopic sections prepared on the LKB-7A ultra-microtome (LKB, Sweden) and contrasted by uranilacetate and lead cytrate.

Mast cells were selectively stained with 1% solution of toluidine blue (Fluka) in 0,5 M HCl, with pH—0.5 (8,9).

To study the proliferative activity of cells, the mice's monoclonal antibodies to the proliferating cell nuclear antigen —PCNA— diluted at 1:50 (clone PC 10, Calbiochem, the USA), and avidin-biotin-peroxidase set for revealing the mice's immunoglobulins (Vectastain, the USA), were used.

Serotonin-positive cells were revealed with the help of polyclonal rabbits' antibodies to serotonin (Ready-to-Use) and streptavidin-biotin-peroxidase set (BjoGenex, the USA). To reveal MTL-positive cells, were used rabbits' antibodies to metal-tioneins (1–2000).

Immunohistochemical identification of antigenes at the histological sections was made according to the main requirements to immune-peroxydase methods (10,11).

The quantity research was conducted with the help of the system of computer analysis of microscopic images— IMSTAR (Imstar, France)—the Morphostar-2 and Colquant-2 license applied software were employed, in accordance with the general principles of stereology in morphometry (12, 13). For each animal, the calculation of corresponding structures was made In ten visual eye sights by three sections of the studied organ. The mitotic index ($1_{mit}$) and the index of proliferating ability ($I_{pcna}$) of the duodenum cells were defined in 10–15 standard sections of crypts, with the overall contents of not less than 1000 nuclei of enterocytes. The test area for finding serotonin-positive and mast cells covered not less than 3 $mm^2$. MML-positive cells were counted in 100 duodenum crypts.

Against the background of ionizing radiation, on the eighth day, a partial—in many cases almost total— restoration of enterocytes' ultra-structure is observed, however, there still occur hyperplasia ("swollen") mytochondria, edema of endoplasmic reticulum, and focal vacuolization of cytoplasm, endocrine cells looking practically unchanged by that time.

Figure 1:
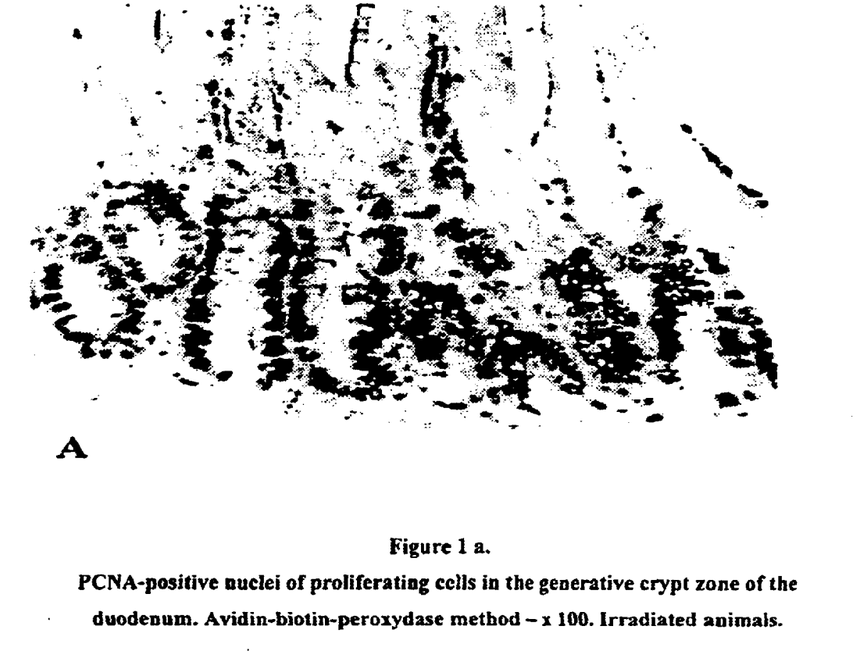
FIG. 1A shows a PCNA-positive nuclei of proliferating cells in the generative crypt zone of the duodenum. Avidin-biotin-peroxydase method—×100. Irradiated animal.
FIG. 1B shows a PCNA-positive nuclei of proliferating cells in the generative zone of the duodenum. Avidin-biotine-peroxydase method—×100. Irradiated animals +L-Lys-Glu dipetide.

Quantity changes in the duodenum of the survived animals on the eighth day, after general instantaneous—γ— irradiation of 6 Gy, have the following specific features: $I_{pcna}$ in the intestinal crypts rises up to 46.5%, while the mitotic index rises up to 4,2% (table 5). These data testify to the fact that restoration of the mucous epithelium of the survived animals goes very quickly, while the pool of trunk cells of the intestinal epithelium is in this period at the stage of hyperregeneration (FIG. 1A).

Figure 2A:
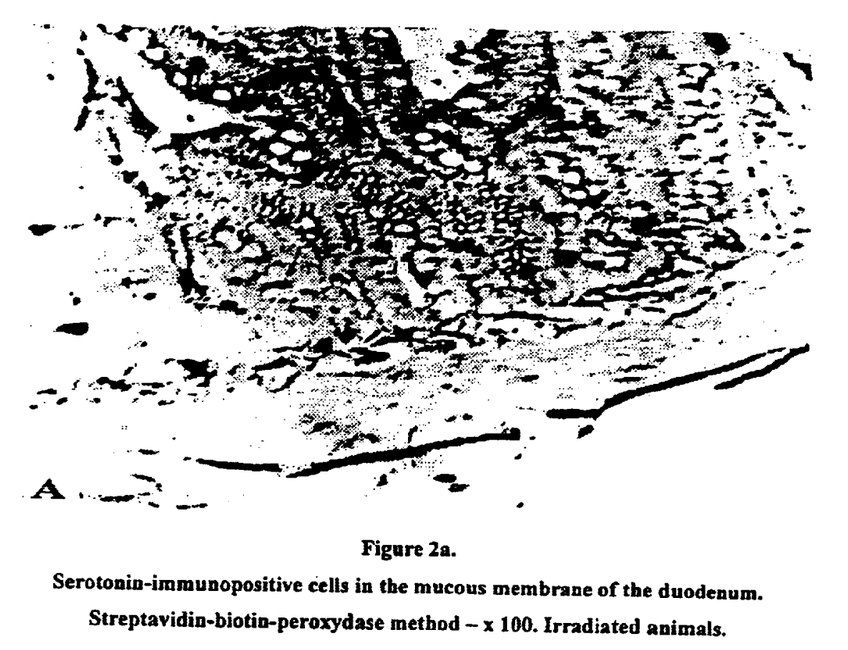
FIG. 2A demonstrates a serotonin-immunopositive cells in the mucous membrane of the duodenum. Streptavidin-biotin-peroxydase method—×100. Irradiated animals.
Figure 2B:
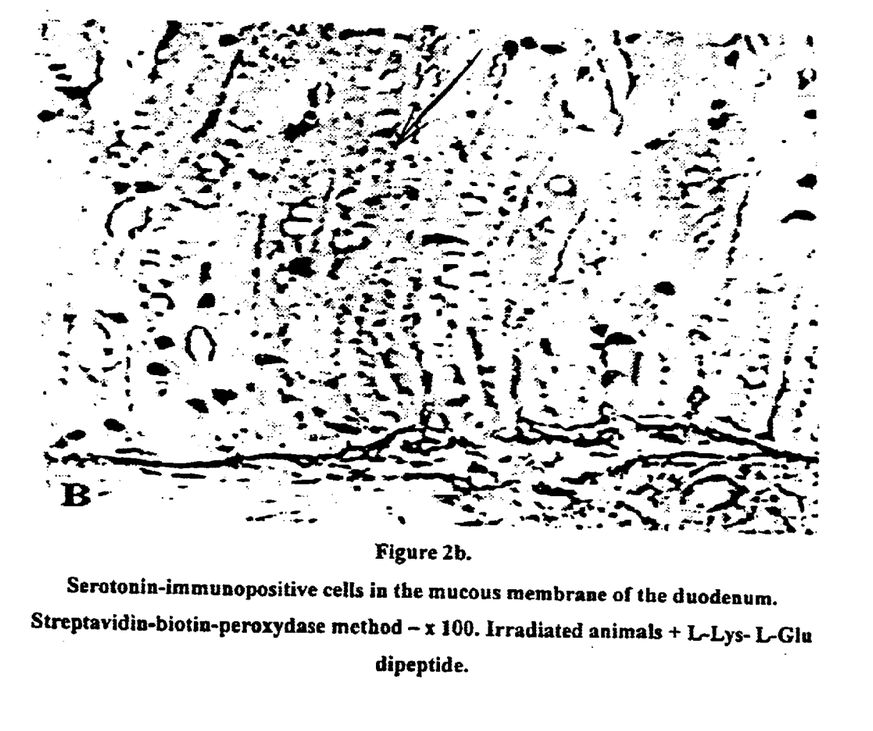
FIG. 2B shows a serotonin-immunopositive cells in the mucous membrane of the duodenum. Streptavidin-biotin-peroxydase method—×100. Irradiated animals +L-Lys-L-Glu dipetide.
Figure 3A:
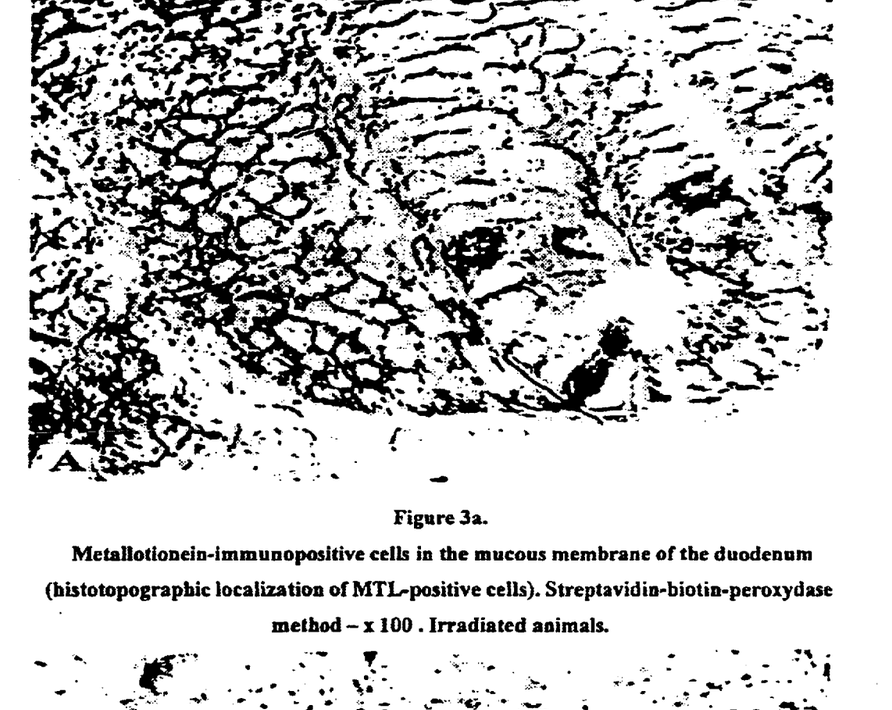
FIG. 3A shows a metallotionein-immunopositive cells in the mucous membrane of the duodenum (histotopographic localization of MLT-positive cells). Streptavidin-biotin-peroxydase method—×100. Irradiated animals.

Histological study of preparations stained with hemat6xilin and eosin also testifies to the start of normalization processes of epithelial architectonics. Computer analysis results, though, show that numerical density of enterochromaffinn cells (FIG. 2A) and MTL-positive cells (FIG. 3A) does not reach yet the indices level of healthy animals.

Figure 4A:
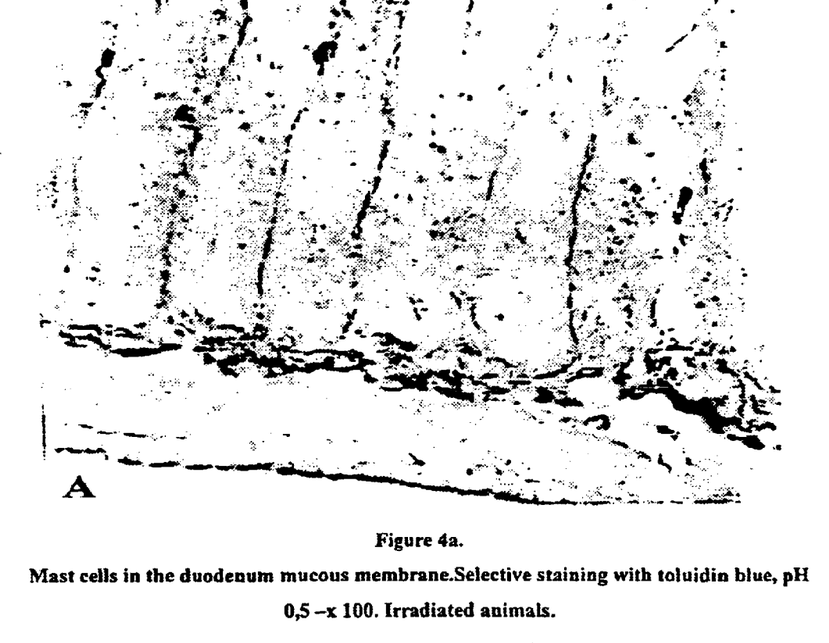
FIG. 4A shows a mast cells in the duodenum mucous membrane. Selective staining with toluidin blue, pH 0.5—× 100. Irradiated animals.
Figure 4B:
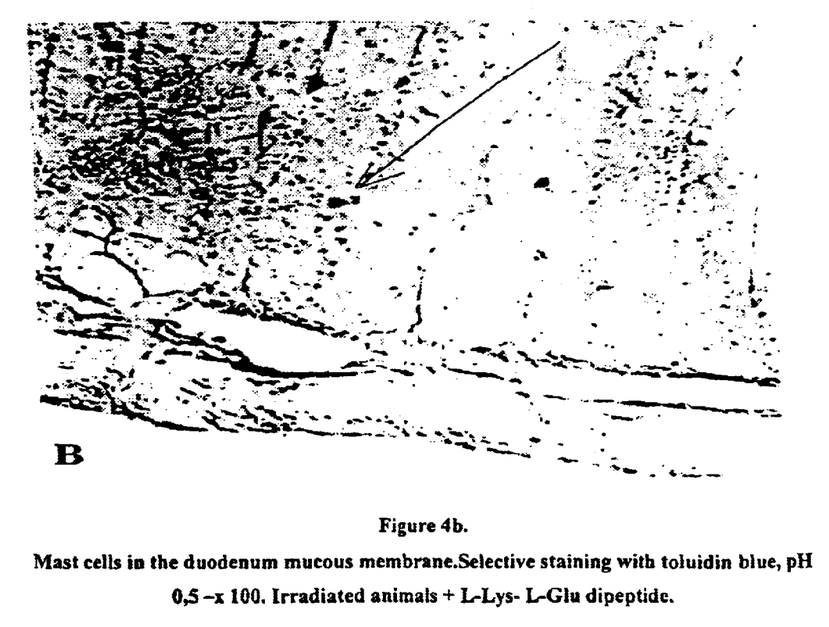
FIG. 4B shows a mast cells in the duodenum mucous membrane. Selective staining with toluidin blue, pH 0.5—× 100. Irradiated animals +L-Lys-L-Glu dipeptide.

The content of mast cells in the mucous plate proper of the irradiated animals is lowered by 10 times (FIG. 4A), which testifies to the uttermost radio-sensitivity of the mucous-type mast cells to the ionizing radiation, as well as to a very slow restoration of their quantity, even when exposed to sublethal doses.

It is noteworthy that the injection of L-Lys-L-Glu dipeptide makes structures of the cytoplasmic reticulum and those, of the plate complex in the duodenum endocrine cells more active, which testifies to its stimulating effect on synthesis processes and hormones secretions.

Figure 3B:
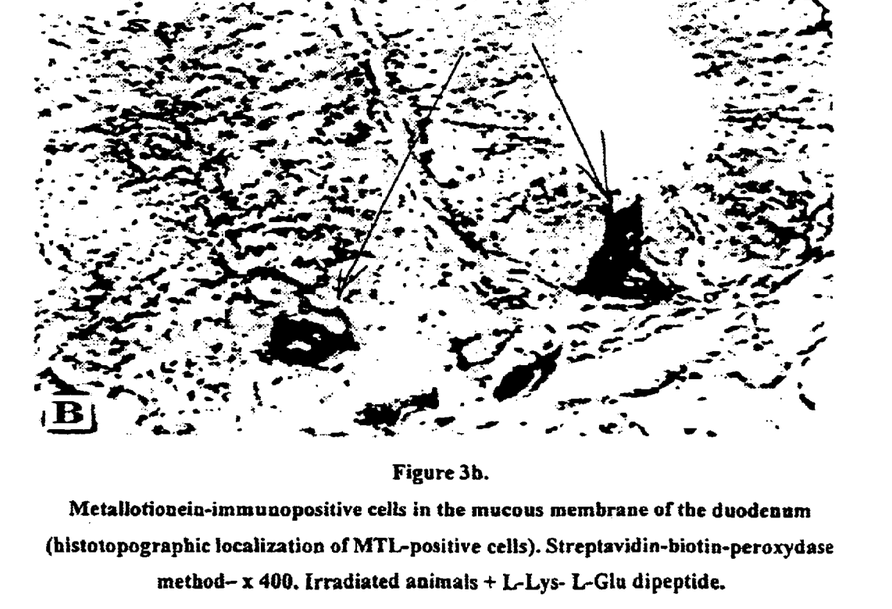
FIG. 3B shows a metallotionein-immunopositive cells in the mucous membrane of the duodenum (histotopographic localization of MLT-positive cells). Streptavidin-biotin-peroxydase method—×400. Irradiated animals +L-Lys-L-Glu dipeptide.

According to the results of the morphometric analysis, in the crypts of the irradiated animals' bowels, after the injection of L-Lys-L-Glu dipeptide, there occurs a considerable acceleration of restoration processes (FIG. 1B). Index PCNA reaches 49.89%, while the mitotic index increases up to 4.7% (table 3). The quantitative density of enterochromaffinn cells practically gets equal to that of healthy animals. There is a tendency to the increase of number and intensity of immune-staining of MTL-positive cells in the crypts' base (FIG. 3B).

Application of L-Lys-L-Glu dipeptide intensifies the proliferative potential of trunk cells of, the bowels and enhances morpho-functional regeneration of the intestinal-mucous after the general instantaneous γ—irradiation with dose of 6 Gy.

Thus, the experimental study proved that L-Lys-L-Glu dipeptide is not toxic, and it activates motabolic processes and proliferative cell activity of any tissue, enhancing their regeneration.

L-Lys-L-Glu dipeptide's features, revealed during the experimental pre-clinical study, allow it to be preserved as a prophylactic and/or treatment used as a stimulator of tissue regeneration for pyo-inflammatory diseases, post-operation complications, trophic disorders, skin & mucous injuries and diseases, radiation, thermal and chemical after-effects, accompanied by a disorder of repair processes.

The examples of the claimed dipeptide's clinical studies, presented below. demonstrate its pharmacological characteristics and confirm its patentability.

EXAMPLE 6

Effectiveness of L-Lys-L-Glu Dipeptide's use as a Treatment for Inflammation of Salivary Glands and Sialolithic Disease 45 patients were being observed. Of these, 27 people had inflammations of the salivary glands, 4 of whom had parotitis. 18 people suffered sialolithic disease of the submandibular gland. The average age of the patients was 35–40. All the patients with the sialolithic disease had the stones extracted. 30 patients (15 of them had inflammation of the salivary gland and the other 15 had sialolithic disease) underwent daily intramuscular injections of L-Lys-L-Glu dipeptide 1 μkg. for 5 days.

The patients of the control group underwent standard treatment: antibacterial, desensitization therapy, iodine-dimexid dressings, physical therapy (ultrasonics, 5–10% potassium iodide electrotherapy on the gland area), local treatment (washing the glands with the solution of antiseptics and antibiotics).

The patients who had sialolithic disease and were treated with L-Lys-L-Glu dipeptide stopped having the discharge of pus from the gland ducts, in the post-operation period the wound in the mouth cavity was healed with the first injection without any after-effects. Swelling and infiltration of soft tissues and mucous membrane of the mouth cavity were resolved on the third fourth day after the operation. The gland reduced in size considerably, and pains stopped.

The patients who had inflammation of the salivary gland and were treated with L-Lys-L-Glu dipeptide, on the fourth-fifth day after the treatment, stopped having pains in the gland and the discharge of pus from the gland ducts, their salivation increased, the swelling and infiltration of the soft tissues were resolved. When palpated, the gland reduced in size considerably and became painless. The patients' general state improved. Their laboratory tests normalized as well.

Thus, the use of L-Lys-L-Glu dipeptide helped reduce the number of inflammations, facilitated regeneration of wounds, and shortened the period of treatment.

EXAMPLE 7

Effectiveness of L-Lya-L-Glu Dipeptide's use as a Treatment for Pyo-inflammatory Diseases of Different Localization L-Lys-L-Glu dipeptide was used in the complex treatment of 15 patients who had flesh sluggish-granulating wounds in lower and upper extremities and 19 patients who had phlegmon of the maxillofacial zone. 1 μkg of the preparation was injected intramuscularly, every day during ten days. Effectiveness of the treatment was evaluated in dynamics according to the changes in activity of wound enzymes and time of healing.

It was found that L-Lys-L-Glu dipeptide proved the most efficacious with the patients with low activity of wound proteoclastic enzymes in the first and second stages of wound process, with necrotic type of cytograms and slow healing. L-Lys-L-Glu dipeptide increased the activity of wound ferments in the first phase of the wound process, causing adaptation restructuring in the wound, and which empowered the synthesis of acid phosphatase in histiocytes, alkaline phosphatase in leukocytes and C cytochrome in macrophagi, intensifying the repair processes. Injecting the dipeptide helped to accelerate clearance of the wounds from necrotic tissues and heal the wounds due to macrophagi, fibroblasts, and leukocytes activation in the inflammation nidus.

L-Lys-L-Glu dipeptide treatment resulted in the faster liquidation of a local inflammatory process, improvement of the general state of patients, and in reduction of the treatment period.

EXAMPLE 8

Effectiveness of L-Lys-L-Glu Dipepilde's use for Cancer Patients With Post-operative Complications L-Lys-L-Glu dipeptide was used in the complex treatment of 9 patients who had sluggish-granulating wounds after the surgical treatment for pulmonary cancer of the $2^{nd}$–$3^{rd}$ stages and 5 cancer of the stomach patients of the $2^{nd}$–$3^{rd}$ stages.

In the pre-operation period, the patients underwent a radical-scheme, radiation therapy employing large fields of complex configuration on the linear electron accelerator (its power is 4,3 Mev) and gamma-therapy device "Rokus-M" in the brake mode. In particular cases, one of the components of the combined treatment was chemotherapy.

Beginning from the third day after the operation, 1 μkg of L-Lys-L-Glu dipeptide was injected intramuscularly daily during 10 days.

It was found that the use of the preparation helped to reduce edema and pain in the wound area, and accelerate both clearance of the wounds from necrotic tissues and forming the post operation cicatrix. During the period of injections, the following factors were observed: normalization of temperature, improvement of appetite and quicker weight gain.

Thus, the use of L-Lys-L-Glu dipeptide as a part of complex treatment of cancer patients stimulates repair processes in the tissues, promotes improvement of the general state of patients and reduces the time of their treatment.

Clinical application of L-lysil-L-glutamic acid (L-Lys-L-Glu) confirmed the data obtained from experimental study that the preparation is an efficacious remedy against the disorder of repair processes.

REFERENCES

1. M. Malinivsky Medicinal substances. In two parts./ Moscow:Medicine. 1993-Part 2.-page 161–191.
2. SERVA—Catalog.—Heidelberg, 1987/88.-PE 1-PE40.
3. Patient of the Russian Federation N 2080120 "Medicinal substance possessing immunemodulating activity". BIN 15.27.05.97.
4. H. D. Yakubke, X. Eshkait Aminoacids, peptides, proteins: Transl. From German/Moscow, Mir. 1985. Page 456.
5. V. Balin, D. Madai, D. Tsvigailo. Local treatment of purulent surgical skin and subcutaneous fat diseases in the conditions of regulated activity of wound enzymes./ St.Petersburg, 1996.
6. V. Kolodin, O. Kuznetsov Quantitativ cytochemical revealing of enzymes in the cell culture after the Rowse virus ifecting//Vopr. Oneol. (Problems in oncology)-1975-Vol.2 1, N9-page 65–71.
7. M. Berston Histochemistry of Enzimes.—Moscow, Mir, 1965-page 464.
8. Enberback L., Miller H. R. P. , Mayrhofer G. Methods for identification and characterization of mast cells by light microscopy//Mast cell differentioation and heterogeneity/Eds. A. D. Beifus et. Al Raven Press, New York, 1986 page 405–416.
9. Stead R. H., Dixon M. F, Braamwell N. H. Mast cells are closely apposed to nerves in the human gastrointestinal mucosa//Gastroenterology.-1987-Vol.87. -page 575–585.
10. Polack G., van Norden S. Introduction into immunocytochemistry: moden methods and problems: Transl. From English-Moscow, Mir, 1987-page 74.
11. Kvernoy I., Yuzhakov V. Staining endocrine tissue and elements of APUD—system//Microseopic technique:Manual/Eds. D. Sarkisov, Y. Perov—Moscow, Medicine, 1966 page 375–418.
12. G. Avtandilov. Medical morphometry. Manual. Moscow, 1990.-page 384.
13. Weibel E. R., Kistler G. S., Scherie W. F., practical stereological methods for morphometric cytology// J.Cell Biol.-1966-Vol.30-page 23–38.

TABLE 1

Influence of L-Lys-Glu dipeptide on the dynamics of cellular elements and structures in rabbits with purulent incised crushed wounds of the soft tissues.

| Groups of animals | Terms of observation (days) | Cellular elements and structures (conventional points) | | | | |
|---|---|---|---|---|---|---|
| | | Fibroblasts | Histiocytes | Leukocyles | Macrophases | Necrosis |
| Control | 6 | 2 | 3 | 5 | 2 | 5 |
| | 14 | 3 | 3 | 5 | 2 | 4 |
| | 21 | 4 | 4 | 4 | 3 | 4 |
| | 28 | 4 | 4 | 2 | 3 | 2 |
| | 40 | 4 | 4 | 2 | 5 | 2 |
| Dipeptide L-Lys-L-Glu | 6 | 4* | 4 | 5 | 3 | 3* |
| | 14 | 5* | 5* | 5 | 3 | 2* |
| | 21 | 5 | 5 | 4 | 2 | 2* |
| | 29 | 5 | 4 | 4* | 2 | 1 |
| | 40 | 6* | 6* | 2 | 2* | 1 |

*$P < 0.05$ as compared to the indices in animals of control group.
Notes;
1 point - absent;
2 points - single (traces);
3 points - few;
4 points - diffuse (moderately);
5 points - many-,
6 points - very many.

TABLE 2

Influence of L-Lys-L-Glu dipeptide on the activity of tissue enzymes in rabbits with purulent incised crushed wounds of the soft tissues.

| Group of animal | Terms of Observation (days) | Acid phosphotase in histiocytes (Conv. Points) | Alcaline phosphotase in leukocytes (Conv. points) | Alcaline phosphotase in vessels (Conv. points) |
|---|---|---|---|---|
| Control | 6 | 3 | 3 | 2 |
| | 14 | 4 | 4 | 4 |
| | 21 | 4 | 4 | 3 |
| | 28 | 3 | 5 | 3 |
| | 40 | 3 | 5 | 2 |
| Dipeptide | 6 | 5* | 6* | 6* |
| L-Lys-L-Glu | 14 | 6* | 6* | 5 |
| | 21 | 5 | 5 | 5* |
| | 28 | 5* | 6 | 4 |
| | 40 | 5* | 5 | 4* |

*$P < 0.05$ as compared to the indices in animals of control group.
Notes;
1 point - absent;
2 points - single (traces);
3 points - few;
4 points - diffuse (moderately);
5 points - many-;
6 points - very many.

TABLE 3

Influence of L-Lys-L-Glu dipeptide on the duration of the wound process in rabbits with purulent incised crushed wounds of the soft tissues.

| Groups of animals | Terms of tile onset of necrotizing tissue rejection form the wound surface | Terms of complete clearance of the wound surface from necrotizing tissues (days) | Terms of the wound epithelization (days) |
|---|---|---|---|
| Control | 12.9 + −1.2 | 21.1 + −3.2 | 31.8 + −1.7 |
| L-Lys-L-Glu dipeptide | 8.3 + −1.1* | 14.2 + −1.3* | 24.9 + −1.9* |

$P < 0.05$ compared to the indices of control animals

TABLE 4

Influence of L-Lys-L-Glu dipeptide an the number of dividing cells in the rats' regenerating liver 32 and 96 hours after the partial hepatectomy (% of the total number of liver cells).

| Groups of animals | Period of research | | Mitotic index | % of cells in the phase of DNA synthesis | Total number of dividing cells |
|---|---|---|---|---|---|
| Healthy animals + sodium hydrochloride | | | 0.682 ± 0.013 | 1.752 ± 4.463 | 3.403 ± 0.498 |
| Control (paixial hepatectomy + sodium hydrochloride) | 32 hours | Before | 0.431 ± 0.019 | 1.043 ± 0.127 | 1.474 + 0.143 |
| | | After | 1.364 + 0.595 | 2.063 ± 0.474 | 3.427 ± 1.066 |
| | 96 hours | Before | 0.417 ± 0.053 | 0.924 ± 0.091 | 1.342 ± 0.060 |
| | | After | 2.012 ± 0.146* | 3.417 ± 0.295 | 5.429 + 0.3880 |
| Partial hepatuctomy + L-Lys-L-Glu dipeptidoe | 32 hours | Before | 0.450 ± 0.067 | 0.870 ± 0.100 | 1.320 + 0.159 |
| | | After | 2.314 ± 0.4611* | 3.882 ± 0.8391" | 6.196 ± 1.279** |
| | 96 hours | Before | 0.294 ± 0.084 | 0.982 ± 0.141 | 1.276j − 0.128 |
| | | After | 4.846 ± 0.334*& | 4.664 ± 1.315** | 9.510 ± 1.609*# |

*P < 0.001 compared to pre-operation indices;
**P < 0.05 compared to pro-operation indices;
&P < 0.001 compared to the indices of the control group animals;
< 0.05 compared to the indices of the control group animals.

TABLE 5

Influence of L-Lys-L-Glu dipeptide on the quantity characteristics of the main parameters of regeneration In rats' duodenum, based on the data of computer analysis of morphological images.

| Groups of animals | $I_{mit}$, % | $I_{PCNA}$, % | $P_{ser}$, % | $N_{MC}/1$ mm$^2$ | $N_{MT}/100$ crypts |
|---|---|---|---|---|---|
| Healthy animals | 2.9 ± 0.1 | 44.8 ± 0.2 | 0.64 ± 0.02 | 169 ± 23 | 132 ± 8 |
| Control irradiated animals + physiological solution) | 4.2 ± 0.4* | 46.5 ± 0.7* | 0.43 ± 0.08* | 18 ± 2* | 75 ± 80 |
| Irradiated animals + L-Lys-L-Glu dipeptide | 4.7 ± 0.1 | 49.8 ± 0.7** | 0.71 ± 0.09 | 24 ± 3* | 102 ± 9* |

*P 4 0.05 in comparison to indices of the healthy animals;
**P < 0.05 in comparison to the indices of the control group.
Notice:
$I_{mit}$ is the mitotic index (%) = $N_{mit}/N_{total} \times 100$
$I_{PCNA}$ is the index of cell proliferative ability-PCNA (%)-Npcna/Ntotal × 100,
Pser is the volume density of serotonin-immunopositive cells (an integal index of serotonin-immunopositive cells content in the tissue volume (%);
NMC/1 square mm is the quantity of mast cells/1 square mm;
NMT/100 crypts is the quantity of L-positive cells in 100 intestine crypts.

What is claimed is:

1. A method of prophylaxis and/or treatment of diseases requiring stimulation of tissue regeneration in a patient in need thereof, comprising
administering to said patient a pharmaceutical peptide preparation containing an effective quantity of L-Lys-L-Glu dipeptide or its salts in a dose of 0.01–100 μkg per 1 kg of weight, at least once a day during a period necessary for stimulation of tissue regeneration, wherein said tissue regeneration occurs during a healing process selected from the group consisting of healing of a purulent incised crushed wound of the soft tissue, healing of liver tissue after its partial hepatectomy, healing of intestinal mucous membrane after radiation injury, and wound healing.

2. A method in accordance with claim 1, where the preparation is administered parenterally, intranasally, orally, or, locally.

3. A method of stimulating tissue regeneration in injured tissue, comprising,
exposing said injured tissue to a pharmaceutical peptide preparation containing an L-Lys-L-Glu dipeptide or its salts in an amount sufficient to promote tissue regeneration in said injured tissue, wherein said injured tissue is selected from the group consisting of purulent incised crushed wounds of the soft tissue, liver tissue after its partial hepatectomy, intestinal mucous membrane after radiation injury, and wounds.

4. A process for the manufacture of a peptide preparation for prophylaxis and/or treatment of diseases requiring stimulation of tissue regeneration, comprising the step of, combining an effective dosage of L-lysyl-L-Glutamic acid dipeptide (L-Lys-L-Glu) or one of its salts with a pharmaceutically admissible carrier to form the peptide preparation for the use in stimulation of tissue regeneration wherein said tissue regeneration occurs during a healing process selected from the group consisting of healing of a purulent incised crushed wound of the soft tissue, healing of liver tissue after its partial hepatectomy, healing of intestinal mucous membrane after radiation injury, and wound healing.

5. The process according to claim 4, wherein said salt is an amino group salt selected from the group consisting of acetate, hydrochloride, and oxalate.

6. The process according to claim 4, wherein said salt is a carboxyl group salt selected from the group consisting of sodium, potassium, lithium, calcium, zinc, magnesium, organic cations, non-organic cations, ammonium and triethylammonium.

7. The process according to claim 4, wherein the peptide preparation is formulated for administration via a means selected from the group consisting of parenteral, intranasal, oral, or topical.

8. The process according to claim 4, wherein the dosage of the dipeptide or its salts is in the range of 0.01 to 100 μg per kg of bodywieght of a patient.

* * * * *